United States Patent [19]

Roduit et al.

[11] Patent Number: 5,250,689
[45] Date of Patent: Oct. 5, 1993

[54] PROCESS FOR THE PRODUCTION OF 2-(METHYLTHIO)-DISODIUM BARBITURATE

[75] Inventors: Jean-Paul Roduit, Sierre; Marcel Etzensperger, Gamsen; Alain Wellig, Ried bei Morel, all of Switzerland

[73] Assignee: Lonza, Ltd., Gampel/Valais, Switzerland

[21] Appl. No.: 936,205

[22] Filed: Aug. 27, 1992

[30] Foreign Application Priority Data

Aug. 30, 1991 [CH] Switzerland ............ 2555/91

[51] Int. Cl.$^5$ .......................... C07D 239/02
[52] U.S. Cl. .................................. 544/299
[58] Field of Search ......................... 544/299

[56] References Cited

U.S. PATENT DOCUMENTS 4,692,524 9/1987 Hassig .................. 544/303

FOREIGN PATENT DOCUMENTS 0411276 2/1991 European Pat. Off. .
0411277 2/1991 European Pat. Off. .

*Primary Examiner*—Cecilia Tsang
*Attorney, Agent, or Firm*—Fisher, Christen & Sabol

[57] ABSTRACT

A process for the production or 2-(methylthio)-disodium barbiturate. Thiourea, malonic acid dimethyl ester and sodium methanolate are reacted to disodium thiobarbiturate. The disodium thiobarbiturate then is reacted with methyl bromide, optionally in the presence of a base, to the end product.

18 Claims, No Drawings

PROCESS FOR THE PRODUCTION OF 2-(METHYLTHIO)-DISODIUM BARBITURATE

BACKGROUND OF THE INVENTION

1. Field of the Invention

The invention relates to a process for the production of 2-(methylthio)-disodium barbiturate of the formula:

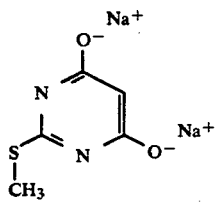

starting from thiourea, malonic acid dimethyl ester and sodium methanolate.

2. Background Art 2-(Methylthio)-disodium barbiturate is an important intermediate product for the production of the herbicide difluoromethyl thiobarbiturate (U.S. Pat. No. 4,692,524).

The production of monosodium thiobarbiturate starting from malonic acid dimethyl ester, thiourea and sodium methanolate is known. These three initial materials are used in an approximately molar ratio of 1:1:1 (European Published Patent Application No. 411,277). In addition the next stage, that is, the methylation of this monosodium thiobarbiturate with methyl bromide to 2-(methylthio)-barbituric acid, is known and this reaction is performed under increased pressure (European Published Patent Application No. 411,276).

A drawback of this two-stage synthesis for the production of 2-(methylthio)-barbituric acid is that in the first stage the monosodium thiobarbiturate is formed, and then, in the next stage, the latter reacts only under increased pressure and higher temperature with methyl bromide to 2-(methylthio)-barbituric acid. A further drawback is that 2-(methylthio)-barbituric acid cannot be converted directly into difluoromethyl thiobarbituric acid but only by an intermediate stage.

BROAD DESCRIPTION OF THE INVENTION

The main object of the invention is to eliminate the above-mentioned prior art drawbacks and to provide a process feasible on an industrial scale in which both stages can be performed without pressure and in which 2-(methylthio)-disodium barbiturate is obtained in good yield, which can be directly converted into difluoromethyl thiobarbituric acid. Other objects and advantages of the invention are set out herein or are obvious herefrom to one skilled in the art.

The objects and advantages of the invention are achieved by the process of the invention.

The invention involves a process for the production of 2-(methylthio)-disodium barbiturate of the formula:

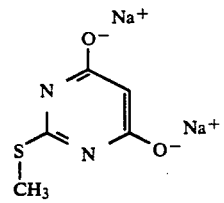

The process includes, in the first stage, reacting thiourea, malonic acid dimethyl ester and sodium methanolate, in methanol, to disodium thiobarbiturate. The latter is reacted in the second stage with methyl bromide, optionally in the presence of a base, to the end product according to formula I.

Preferably the reaction in the first stage is performed either under normal pressure or at a pressure of 2 to 4 bars. Preferably the reaction in the first stage is performed with 2 to 4 mol of sodium methanolate. Preferably the reaction in the first stage is performed at temperatures of 65° to 100° C. Preferably the reaction in the second stage is performed in a polar solvent, optionally in a polar solvent mixture. Preferably the reaction in the second stage is performed at temperatures of 0° to 20° C. Preferably, in the second stage, an alkali metal hydroxide is used as the base. Preferably the reaction in the second stage is performed under normal pressure. Preferably the two reaction steps comprising the invention process are performed without isolation of the intermediate product.

DETAILED DESCRIPTION OF THE INVENTION

According to the invention the process is performed so that, in the first stage, thiourea, malonic acid dimethyl ester, and sodium methanolate, in methanol, are reacted to disodium thiobarbiturate and the latter is reacted in the second stage with methyl bromide, optionally in the presence of a base, to the end product according to the formula:

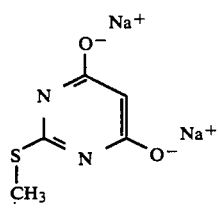

The reaction in the first stage is suitably performed with 2 to 4 mol of sodium methanolate, preferably with 3 mol, relative to 1 mol of thiourea and 1 mol of malonic acid dimethyl ester. The reaction in the first stage can take place either in an autoclave under a pressure of 2 to 4 bars, or under normal pressure. Suitably the reaction in the first stage is performed at a temperature of 65° to 100° C., preferably under reflux.

After a usual reaction time of 3 to 5 hours the disodium thiobarbiturate can then be isolated either in a manner usual to one skilled in the art or it can be used directly for the second stage.

The reaction in the second stage is suitably performed with somewhat of an excess of methyl bromide. Preferably 1 to 1.3 of mole methyl bromide relative to 1 mol of disodium thiobarbiturate is used. The reaction in the second stage is optionally performed in the presence of a base. Suitably an alkali metal hydroxide is used as the base. As alkali metal hydroxide, for example, sodium hydroxide or potassium hydroxide is used. Suitably the reaction in the second stage is performed in a polar solvent, optionally in a polar solvent mixture. Water, low boiling alcohols, such as, methanol, ethanol and isopropanol, or low boiling ketones, such as, acetone, can be used as the polar solvents. As the polar solvent mixture, a water-alcohol or water-ketone mixture, such as, a water-isopropanol or water-acetone mixture, can be used. The reaction temperature in the second stage is suitably between 0° and 20° C., preferably between 5° and 15° C. Suitably the reaction in the second stage is performed under normal pressure.

After a usual reaction of 2 to 3 hours in the second stage, the end product according to formula I can be isolated, for example, by filtration.

In a preferred variant the process is performed without isolation of the intermediate product (disodium thiobarbiturate) and then the end product according to formula I is obtained after a usual reaction time of 2 to 3 hours.

EXAMPLE 1

(a) Production of disodium thiobarbiturate (with pressure)

In an autoclave (2 l) a 30 percent methanolic solution of sodium methanolate (432.2 g, 2.4 mol) was introduced under an inert atmosphere and diluted with methanol (200 g, 6.24 mol). Then thiourea (60.8 g, 0.8 mol) and malonic acid dimethyl ester (105.7 g, 0.8 mol) were added and all of this was heated with stirring to 100° C.—an adjustment to a pressure of 3 bars had taken place. After 3 hours the reaction mixture was cooled to 2° C. and the disodium thiobarbiturate was isolated by filtration in the form of white crystals. 244 g of moist product was isolated. The methanol in the filtrate was recovered by distillation.

(b) Production of 2-(methylthio)-disodium barbiturate 244 g of disodium thiobarbiturate was dissolved in water (550 g). Undissolved particles were removed by filtration. Then the resultant filtrate was cooled to 5° C. Then a 40 percent aqueous sodium hydroxide solution (87.6 g, 0.876 mol) and isopropanol (65 g, 1.08 mol) were added. To this a previously prepared solution of methyl bromide (83.25 g, 0.876 mol) in isopropanol (249.75 g, 4.155 mol) was added within 3 hours. Then the reaction mixture was stiffed for another hour at 10° C. and within 20 min. mixed with isopropanol (194 g, 3.22 mol) during the cooling to 1° C. This mixture was kept for another 15 min. at 1° C. After filtration, 249.8 g of moist product in the form of white crystals, corresponding to a yield of 90.5 percent relative to the disodium thiobarbiturate used, was obtained. 237.13 g of the thus obtained 2-(methylthio)-disodium barbiturate was then dissolved in water (239 g) at 45° C. Then isopropanol (237 g, 3.94 mol) was added within 10 to 15 min at 45° C. with stirring, and the product began to crystallize out. The thus obtained white crystalline product was filtered and dried at 65° C. and a pressure of 0.026 bar. After crystallization, 134.5 g of dry crystalline material was obtained with a 95.2 percent content of 2-(methylthio)-disodium barbiturate, corresponding to a yield of 83.5 percent, relative to the thiourea used.

EXAMPLE 2

(one-pot variant)

(a) Production of disodium thiobarbiturate (without pressure)

72 kg of thiourea (947 mol) was dissolved in anhydrous methanol (182 l). Then malonic acid dimethyl ester (125 kg, 947 mol) and sodium methanolate (717 kg, 2840 mol) 21.4 percent in methanol were added and all of this was stirred under reflux for 3 hours. Then it was cooled and the methanol was distilled off under vacuum. After addition of distilled $H_2O$ (360 l), the remaining amounts of methanol were distilled off under vacuum.

(b) Production of 2-(methylthio)-disodium barbiturate 30 percent sodium hydroxide solution (104.1 l) and acetone (767 l) were added to this mixture. Then methyl bromide at 10° C. (98.5 kg, 1036 mol) was added over 2.5 to 3 hours. Then it was stirred at 15° C. for another 2.5 hours. Altogether, after filtration at 0° C., 318.6 kg of moist 2-(methylthio)-disodium barbiturate (97 percent) was obtained, corresponding to a yield of 82.7 percent, relative to the thiourea used.

We claim:

1. Process for the production of 2-(methylthio)-disodium barbiturate of the formula:

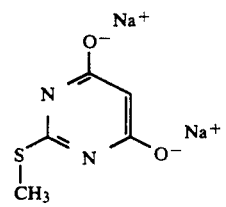

characterized in that, in the first stage, thiourea, malonic acid dimethyl ester and sodium methanolate, in methanol, are reacted to disodium thiobarbiturate and, in the second stage, the latter is reacted with methyl bromide to the end product according to formula I.

2. The process according to claim 1 wherein the reaction in the first stage is performed either under normal pressure or at a pressure of 2 to 4 bars.

3. The process according to claim 2 wherein the reaction in the first stage is performed with 2 to 4 mol of the sodium methanolate.

4. The process according to claim 3 wherein the reaction in the first stage is performed at a temperature of 65° to 100° C.

5. The process according to claim 1 wherein the reaction in the second stage is performed in at least one polar solvent.

6. The process according to claim 5 wherein the at least one polar solvent is a polar solvent mixture.

7. The process according to claim 5 wherein the reaction in the second stage is performed at a temperature of 0° to 20° C.

8. The process according to claim 7 wherein the reaction in the second stage is conducted in the presence of a strong base.

9. The process according to claim 8 wherein, in the second stage, an alkali metal hydroxide is used as the base.

10. The process according to claim 9 wherein the reaction in the second stage is performed under normal pressure.

11. The process according to claim 8 wherein the reaction in the second stage is performed without isolation of the disodium thiobarbiturate from the reaction mixture of the first stage.

12. The process according to claim 1 wherein the reaction in the first stage is performed with 2 to 4 mol of the sodium methanolate.

13. The process according to claim 1 wherein the reaction in the first stage is performed at a temperature of 65° to 100° C.

14. The process according to claim 1 wherein the reaction in the second stage is performed in a polar solvent mixture and in the presence of a strong base.

15. The process according to claim 1 wherein the reaction in the second stage is performed at a temperature of 0° to 20° C.

16. The process according to claim 1 wherein the reaction in the second stage is conducted in the presence of an alkali metal hydroxide.

17. The process according to claim 1 wherein the reaction in the second stage is performed under normal pressure.

18. The process according to claim 1 wherein the reaction in the second stage is performed without isolation of the disodium thiobarbiturate from the reaction mixture of the first stage.

* * * * *